United States Patent
Hynes et al.

(10) Patent No.: US 7,204,810 B2
(45) Date of Patent: Apr. 17, 2007

(54) AUTOGENOUS BONE COLLECTION AND DELIVERY SYSTEM

(75) Inventors: Richard A. Hynes, Melbourne Beach, FL (US); J. Todd Strong, Birmingham, AL (US)

(73) Assignee: SDGI Holdings, Inc., Wilmington, DE (US)

( * ) Notice: Subject to any disclaimer, the term of this patent is extended or adjusted under 35 U.S.C. 154(b) by 178 days.

(21) Appl. No.: 10/335,662

(22) Filed: Jan. 2, 2003

(65) Prior Publication Data
US 2003/0130594 A1    Jul. 10, 2003

Related U.S. Application Data

(60) Provisional application No. 60/345,678, filed on Jan. 2, 2002.

(51) Int. Cl.
*A61B 10/00*    (2006.01)
(52) U.S. Cl. .................................................. 600/562
(58) Field of Classification Search ............... 600/562, 600/564–567; 604/22, 27; 606/168
See application file for complete search history.

(56) References Cited

U.S. PATENT DOCUMENTS

| | | | | |
|---|---|---|---|---|
| 4,314,565 | A | * | 2/1982 | Lee .......................... 600/566 |
| 4,753,634 | A | | 6/1988 | Johnson |
| 4,922,902 | A | * | 5/1990 | Wuchinich et al. ........... 604/22 |
| 5,256,160 | A | | 10/1993 | Clement |
| 6,022,354 | A | | 2/2000 | Mercuri et al. |

FOREIGN PATENT DOCUMENTS

| | | |
|---|---|---|
| DE | 86 09 830 | 8/1986 |
| DE | 94 20 694 | 3/1995 |
| DE | 44 35 927 | 2/1996 |

OTHER PUBLICATIONS

Written Opinion dated Jan. 16, 2004 from PCT/US 03/00078.
International Preliminary Examination Report dated May 21, 2004 from PCT/US 03/00078.
International Search Report dated Oct. 10, 2003 from PCT/US 03/00078.

* cited by examiner

*Primary Examiner*—Max F. Hindenburg
*Assistant Examiner*—Brian Szmal
(74) *Attorney, Agent, or Firm*—Woodard, Emhardt, Moriarty, McNett & Henry LLP

(57) ABSTRACT

A selective filtering collection and delivery system for collecting and delivering autogenous bone to and from a surgical site is provided. The selective filtering collection device includes a suction nozzle, suction nozzle assembly and a vacuum source. Disposed in parallel between the suction nozzle assembly and the vacuum source are a removable filter cartridge and a filter bypass tube. A switch on the suction nozzle assembly may be actuated to provide suction to the suction nozzle through either the bypass tube or through the filter cartridge. When suction is applied through the filter cartridge, autogenous bone is collected on a filter medium within the cartridge. Additionally, the cartridge may be removed and directly placed into a delivery device. The delivery device includes a ratchet system that actuates a plunger base to accurately extrude the bone material from the filter cartridge into the desired surgical location.

16 Claims, 3 Drawing Sheets

AUTOGENOUS BONE COLLECTION AND DELIVERY SYSTEM

REFERENCE TO RELATED APPLICATION

This application claims the benefit of U.S. Provisional Patent Application Ser. No. 60/345,678 filed Jan. 2, 2002, which is hereby incorporated by reference in its entirety.

BACKGROUND OF THE INVENTION

1. Field of the Invention

This invention relates to the field of autogenous bone collection. More particularly, the present invention relates to a device for collecting autogenous bone from a surgical site and extruding the collected bone where desired.

2. Description of the Prior Art

Orthopedic or other surgical procedures involving bone often generate bone chips or particulates that may be harvested and used, for example by implanting the harvested bone back into the patient from which it was derived, as an autogenous graft material. Prior art bone and tissue collection systems are known which include a collection filter disposed in a suction line of the system. In such systems having the filter in the path of the only suction line, suction is removed from the surgical site while the filter medium and/or collected tissue is removed.

Despite some work in the area, there is a need for an autogenous bone collection system that permits the physician to selectively switch between a material capture mode and a material rejection mode without having to remove a bone capture filter from the suction line or from the housing assembly. There is additionally a need for a selective bone capture system wherein the bone capture filter may be removed without pausing the suction applied to the surgical site. There is a further need for a filter cartridge and bone delivery system that reduces the risk of contamination of the collected bone material.

There is also a need for a bone delivery system that accepts a filter cartridge from a filtering system and extrudes the bone material contained therein into the surgical site, even if the bone is highly compressed and dense. There is additionally a need for a delivery system that allows for accurate delivery of the bone tissue to the desired surgical site.

These objects, and others, are addressed by the present invention.

SUMMARY OF THE INVENTION

The present invention provides a bone collection system that has first and second operational modes for selectively collecting or bypassing to waste tissue materials travelling through the system. Thus, one embodiment of the present inventions relates to a bone collection system comprising a vacuum source, a suction nozzle assembly, a filter and a bypass tube. The filter and bypass tube are connected in parallel between the suction nozzle assembly and the vacuum source. The nozzle assembly includes a switch-actuated-valve which connects the suction nozzle to the vacuum source via either the filter or the bypass tube. The filter is desirably incorporated in a removable filter cartridge having an internal chamber for tissue collection, the chamber having an extrusion opening and a variable volume, wherein reduction in the chamber volume extrudes collected tissue materials from the tissue opening. For example, the chamber may have a wall defined by a translatable plunger for reducing the chamber volume.

Another embodiment of the present inventions provides a removable filter cartridge for use in a bone collection system. The removable filter cartridge of this embodiment comprises a housing including an inner chamber, defined by the housing back wall and sidewalls. An exit port is in communication with the inner chamber through the sidewall. A filter medium including mesh sized to capture bone material while permitting fluid passage is located in the inner chamber, in fluid communication with the exit port. A filter cap including an entry port is removably engaged with the front end of the filter cartridge housing. A plunger base is slidably located within the filter cartridge housing and is initially placed against the back wall of the housing. In another embodiment, a bore extends through the back wall of the cartridge housing, adjacent the plunger base.

Another embodiment of the present inventions concerns a bone delivery system for extruding bone collected in a removable filter cartridge. A removable filter cartridge including a plunger base located in the inner chamber of the filter cartridge is positioned in a delivery device. A ram is aligned with a bore through the back wall of the filter cartridge housing. In one particular embodiment, squeezing the delivery device handle advances the ram through the bore and forces the plunger base forward. Bone from the inner chamber is extruded through an opening at the front end of the delivery device.

Related objects and advantages of the present invention will be apparent from the following description.

DESCRIPTION OF THE PREFERRED EMBODIMENTS

Figure 1:
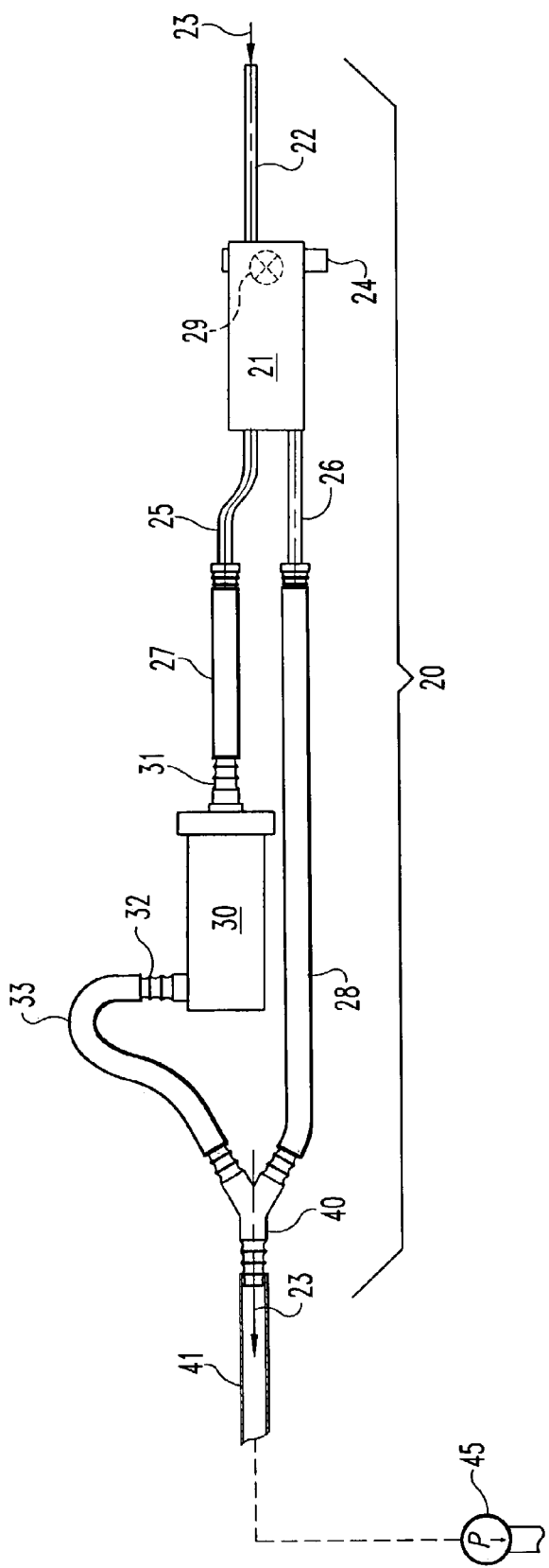
FIG. 1 is a side perspective view of a selective filtering system useful with a bone collection system in accordance with one embodiment of the present inventions.

For the purposes of promoting an understanding of the principles of the inventions, reference will now be made to the embodiments illustrated in the drawings and specific language will be used to describe the same. It will nevertheless be understood that no limitation of the scope of the inventions is thereby intended, such alterations and further modifications of the principles of the inventions as illustrated therein being contemplated as would normally occur to one skilled in the art to which the inventions relate.

In accordance with one embodiment of the present invention, a selective filtering collection device is provided which includes a suction nozzle, suction nozzle assembly and a vacuum source. Disposed in parallel between the suction nozzle assembly and the vacuum source are a filter cartridge and a filter bypass tube. A switch on the suction nozzle assembly may be actuated to provide vacuum to the suction nozzle either through the bypass tube or through the filter cartridge. When vacuum is applied through the filter cartridge, bone material is collected.

Referring now to FIG. 1 there is shown a side view of a selective filtering system 20 for selectively controlling the direction of the suction flow to facilitate the collection of bone. The selective filtering system 20 can be connected to a vacuum pump 45. Selective filtering system 20 includes a suction nozzle assembly 21, connected to which is the suction nozzle 22. Preferred suction nozzle assembly 21 is designed to be held in the hand of a physician during use. A selector switch 24 located on the suction nozzle assembly 21 selectively actuates a valve 29 in the suction nozzle assembly 21 to direct vacuum from pump 45 through one of two discharge openings 25 and 26. Selector switch 24 includes a two position switch, the position of which controls the discharge opening in communication with the suction nozzle 22. Alternatively, selector switch 24 may be a spring-biased switch, which toggles the valve 29 from a first position to a second position while the switch 24 is depressed by the physician. Other types of switches for toggling the valve 29 may be used.

Discharge openings 25 and 26 are connected to filter tube 27 and bypass tube 28, respectively. Filter tube 27 is connected to a bone collection filter cartridge 30 via entry port 31. Another piece of filter tubing 33 is connected to the side exit port 32 of the bone collection filter cartridge 30. Optionally as will be discussed below in connection with FIGS. 2 and 3, the filter cartridge 30 may be a self-contained removable cartridge. Additionally, the filter cartridge 30 is preferably made of a biocompatible material. If plastic is chosen, the filter cartridge 30 may be made of transparent or translucent plastic material that will enable a visual determination of the level of material captured within the filter cartridge 30 without having to open the filter cartridge 30.

Both the filter tube 33 and filter bypass tube 28 are connected to the inputs of the "Y" connector 40. From the "Y" connector, suction line 41 connects the selective filtering system to a vacuum pump 45.

In operation, the selective filtering system 20 permits autogenous bone collection as follows. During a bone drilling or other bone-generating surgical procedure, pump 45 is switched on and vacuum is applied to the system via suction line 41. Fluid containing bone and/or soft tissue is drawn into the suction nozzle 22 of the selective filter system 20 in the direction of arrows 23. According to the physician's desire to retain the material for later use, the selector switch 24 is set by the operator to provide suction to the suction nozzle 22 via either discharge opening 25 or discharge opening 26. When the selector switch 24 is set to one position, vacuum is provided to the suction nozzle 22 via bypass tube 28, from where the material containing fluid is suctioned directly to a waste canister at the vacuum pump 45.

When the selector switch 24 is set to its other position, vacuum is provided to the suction nozzle 22 via filter tubes 27 and 33 and through the filter cartridge 30. The material bearing fluid is then drawn through the bone collection filter cartridge 30. Bone is collected in the bone collection filter cartridge 30 for later use, e.g. for reintroduction to the same or a different surgical site. The waste fluid is suctioned of to the waste container at the vacuum pump 45.

Using the selective filtering system 20 a physician is able to selectively choose when the suction will be filtered for bone retrieval or for waste. By having this choice, the quality of bone collected is much better and has less soft tissue content. Further, the present system advantageously permits the collection filter to be removed from the suction line without disrupting the surgical procedure, as the operator can maintain suction pressure at the suction nozzle 22 even during the removal of the filter by switching the suction path via the selector switch 24. Thus, when a first collection filter is full, it may be exchanged in favor of a new collection filter without substantial disruption of the ongoing procedure.

Figure 2:
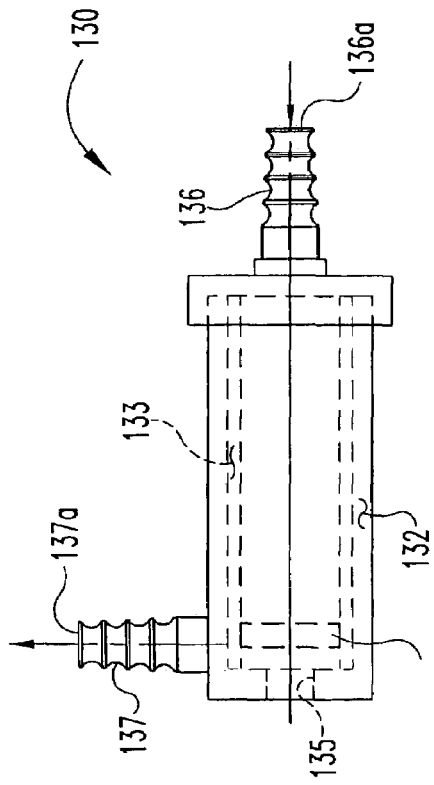
FIG. 2 is a side view of a bone collection filter cartridge that may be used with the selective filtering system of FIG. 1.
Figure 3:
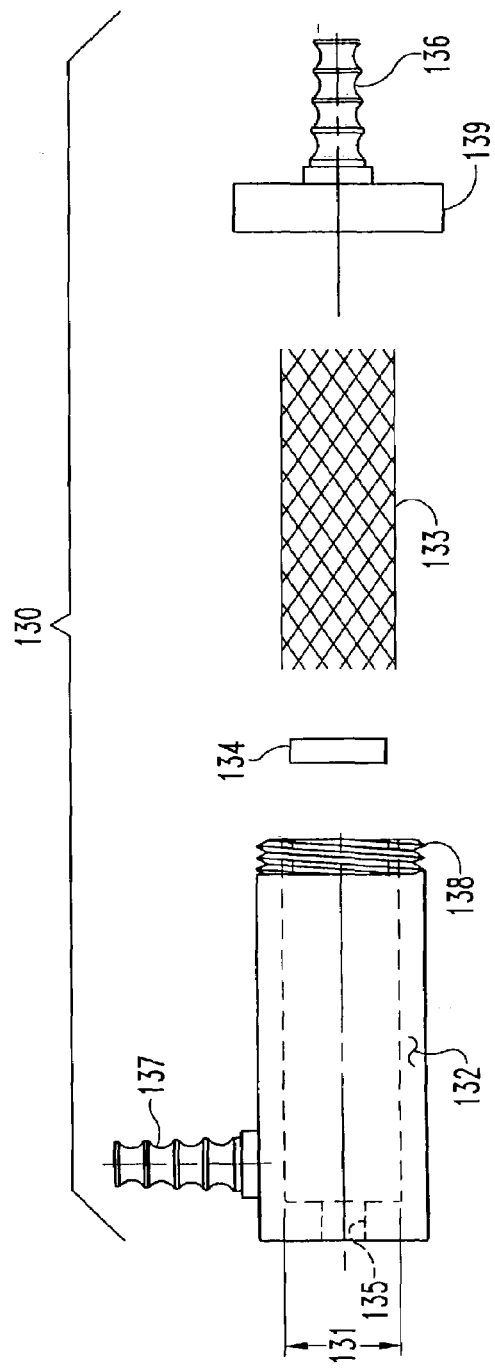
FIG. 3 is an exploded side view of the removable bone collector filter cartridge of FIG. 2.

Referring now to FIG. 2, there is shown a side view of one embodiment of a removable bone collector filter cartridge 130 that may be used as the filter cartridge 30 of the selective filtering system 20 of FIG. 1. FIG. 3 is an exploded view of the filter cartridge of FIG. 2. The removable filter cartridge 130 includes an outer cartridge housing 132 and an inner cartridge filter 133. Outer cartridge housing may be made from a variety of biocompatible metals or plastics, by machining or injection molding. The inner cartridge filter 133 is preferably a mesh material fabricated from metal, polymeric materials or combinations thereof. In the present embodiment, the inner cartridge filter 133 is preferably substantially cylindrical and fitted to the inner chamber 131 of the outer cartridge housing 132, which would also be substantially cylindrical to accept the inner cartridge filter 133. However, this is not meant to be limiting, as other filter and inner chamber cross-sections may be used. The size of the interstices between the filaments of the mesh of the inner cartridge filter 133 can vary depending on the desired use of the filter cartridge 130.

A filter plunger base 134 sits at the base of the filter cartridge 130, inside the inner cartridge filter 133. Filter plunger base 134 is additionally made of a biocompatible material, and may be made of a variety of biocompatible metals or plastics, or more preferably, is made of an elastomeric material having a medium to high durometer hardness. The filter plunger base 134 has a diameter less than the inner diameter of the inner cartridge filter 133, permitting the filter plunger base 134 to slide the entire length of the inner cartridge filter 133, when actuated by the delivery mechanism. Preferably, the diameter of the filter plunger base 134 is just slightly less than the inner diameter of the inner cartridge filter 133 and is similar in shape to the cross-section of the inner chamber 131 of the outer cartridge housing 132. For example, in the present embodiment using a cylindrical inner chamber, a generally circular filter plunger base would be used.

Annular bore or ram aperture 135 is in communication with the filter plunger base 134 through the rear wall of the outer cartridge housing 132. Initially, the aperture 135 is sealed for use during the bone collection process to maintain the sanitary condition of the inner filter cartridge 133 and filter plunger base 134. However, in use, a ram on the delivery device is aligned with the ram aperture 135 and, when advanced by the delivery mechanism, breaks the seal on the ram aperture 135 and advances the filter plunger base 134 through the inner cartridge filter 133.

Additionally the cartridge filter 130 includes a front entry port 136 and a side exit port 137, containing entry and exit apertures 136a and 137a, respectively. The front entry port 136 is located on the removable filter tip 139. Removable filter tip 139 includes a thread (not shown) which mates with thread 138 to secure the filter tip 139 to the outer cartridge housing 132. This is not meant to be limiting, as the removable filter tip may be secured to the filter cartridge housing by other means, such as a snap fit.

Fluid and bone material enter the filter cartridge 130 through the entry aperture 136a, where it passes directly into the inner cartridge filter 133. The inner cartridge filter 133 separates and collects the bone material from the fluid. The fluid portion is diverted out the side exit aperture 137a, through the inner cartridge filter 133. The desired bone material is collected on the inner wall of the inner cartridge filter 133. Additionally, fluid and bone material cannot exit the filter cartridge out the rear aperture 135, due to the filter plunger base 134.

As noted above, other inner chamber cross sectional shapes may be used. For example, if formed using a mold, the cross section of inner chamber 131 may be square or may be partially rounded with one or more flattened sides, etc. In such a case a flat filter screen may be placed in and/or adhered to the flat side of the inner chamber 131 bearing the exit port 137. Additionally, if a flat filter screen is used, a channel may be made in the inner chamber to receive the flat filter screen and maintain the screen in front of the exit port at all times. Alternatively, a square or other shaped inner filter cartridge may be used. Correspondingly, the outer edge of the filter plunger base 134 would be designed to correspond to the cross-section of the inner chamber 131 (i.e., square, partially rounded with one or more flattened sides, etc.) permitting the filter plunger base 134 to slide through the inner chamber 131, extruding bone out the entry end of the filter cartridge 130.

When used in a selective filter system, such as that shown in FIG. 1, if the filter is full or the surgeon determines that there is a need for autogenous bone, the filter cartridge 130 is removed by disconnecting the filter tubes attaching the entry and exit ports of the filter cartridge to the filter system. This can be done without removing suction from the system by switching the suction through the bypass tube of the selective filtering system (bypass tube 28 of FIG. 1). After removing the filter cartridge 130, the entry end cap filter tip 139 of the filter cartridge 130 is unscrewed from cartridge thread 138, exposing the inner filter medium and collected bone for use by the physician.

Figure 4:
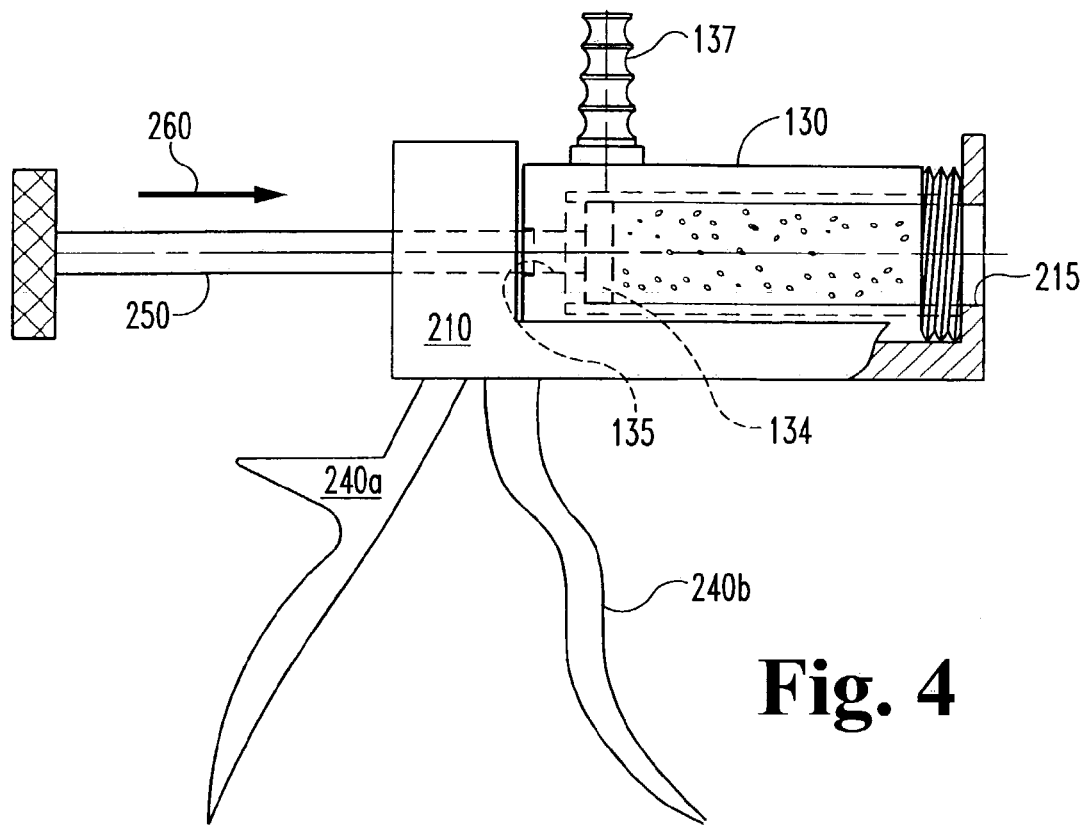
FIG. 4 is a partial side perspective view of a bone collector delivery system including a removable bone collector filter cartridge.
Figure 5:
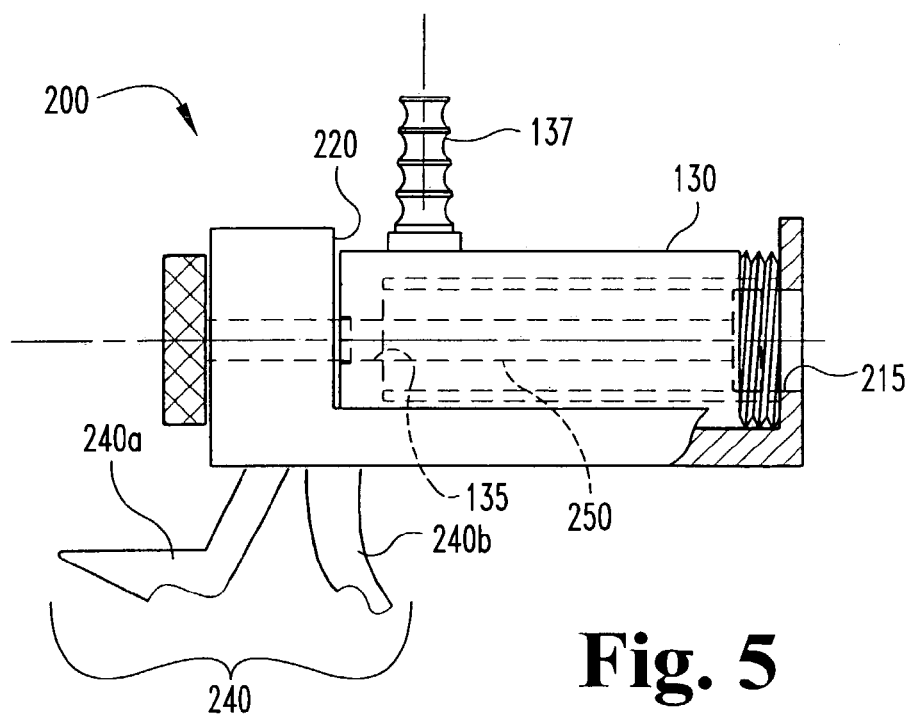
FIG. 5 is a partial side perspective view of a bone collector delivery system including a removable bone collector filter cartridge in the fully extruded position.

Referring now to FIG. 4 there is shown a partial side perspective view of a bone collector delivery device 200 including a removable bone collector filter cartridge, which may be a removable bone collection filter cartridge as described in connection with FIGS. 1, 2 and 3. FIG. 5 is a partial side perspective view of a bone collector delivery system including a removable bone collector filter cartridge in the fully extruded position.

The delivery device 200 includes a delivery housing 210 having a recess 220 therein. Recess 220 is adapted to closely receive a filter cartridge, such as filter cartridge 130. The delivery housing 210 additionally has an extrusion aperture 215 at the distal end in communication with the open end of the filter cartridge 130.

The delivery device 200 additionally includes a ratchet handle 240 and a ram 250. Ratchet handle 240 provides a mechanical advantage in the advancement of the ram 250, and may include ratchet gearing or springs (not shown) which, when the handle members 240a and 240b are grasped and squeezed together, the ratchet gear drives the ram 250 in the direction of arrow 260. When the handle is released, the ram 250 is returned to its resting position.

In operation, the bone collection filter cartridge (30 or 130 of FIGS. 1–3) is disengaged from the selective filtering collection device and the filter tip (139 of FIG. 3) is removed. The inner filter medium need not be removed by the physician, nor does the bone material need to be spooned out. This reduces the risk of contamination of the bone material by reducing the handling of the material used. The filter cartridge is then loaded into the delivery device recess 220. Alternatively, the filter tip 139 (FIG. 3) can be retained in attachment with the filter cartridge, and the delivery device recess 220 adapted to receive the cartridge/filter tip assembly. In this fashion, the filter tip 129 may serve to provide a shape and/or dimension to the bone when extruded from the cartridge as discussed further below. In this regard, the filter tip 129, or another similar filter tip especially designed for the extrusion, can be configured to provide an extruded bone mass optimized for delivery to a given surgical site. For example, for relatively deep surgical sites, the filter tip can provide a small diameter, elongate tube for delivery of the extruded bone mass to the site.

After receiving the filter cartridge 230, the handle 240 of the delivery device 210 is depressed. As the handle 240 is depressed, ram 250 is ratcheted into the cartridge via the sealed cartridge aperture 235 opposite the entry side of the bone collection filter cartridge 230. The ram 250 pushes a plunger base 134 that is located within the inner diameter of the filter medium. As the handle 240 is ratcheted, the bone is extruded through the opening 215 in the housing 210. Opening 215 is in communication with the entry end of the filter cartridge 230, when the filter cartridge is placed in the recess 220. The bone is then extruded back into the surgical site, eliminating the need to use allograft bone, other bone substitute materials, or going to a separate surgical site to harvest additional bone. The delivery device 200 is capable of accurately extruding compressed, dense bone straight from the filter cartridge due to its leveraged ratchet mechanism. After the bone is extricated from the filter, releasing the handle returns the ram 250 on the delivery device to its resting position and the filter cartridge can be removed and discarded.

With reference to all of the Figures, in certain embodiments of the invention, kits are provided containing element(s), potentially disposable element(s), for use with a bone collection device and optionally then with a bone delivery device 200. For example, such kits may include a single, disposable filter cartridge 230, or a plurality of filter cartridges 230 optionally having varying internal volumes suited to collect bone in connection with surgical procedures that generate varying amounts of bone. In this fashion, a physician can assure that the filter cartridge 230 will be substantially filled with bone from the surgical procedure so that an efficient extrusion-delivery operation can be carried out with minimal if any bone waste. Moreover, one or more filter tips 139 can be provided in the kit, and wherein a plurality of tips 129 are provided they may include different tips adapted to extrude differently-dimensioned bone masses. For example, a first filter tip 139 may deliver a relatively large-diameter extruded cylinder, and a second filter tip 139 may be adapted to deliver a relatively small-diameter extruded cylinder. In addition or alternatively, one filter tip 139 may include a relatively short delivery tube, and another may include a relatively long delivery tube (for example to deliver bone to a deep surgical site). The suction nozzle assembly 21 may also be included in such kits, along with any or all of the other components described in FIGS. 1–5.

While the inventions have been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A selective filtering system for collecting tissue, comprising:
   a vacuum source;
   a nozzle for collecting tissue, the nozzle fluidly connected to the vacuum source;
   a first fluid path between the nozzle and the vacuum source, the first fluid path including a removable cartridge containing a filter for filtering tissue, said removable cartridge including a chamber for collecting said tissue, said chamber having an opening and convertible from a first configuration having a relatively larger volume to a second configuration having a relatively smaller volume so as to extrude collected tissue through said opening;
   a second fluid path between the nozzle and the vacuum source, the second fluid path bypassing the filter; and
   a valve for selectively directing tissue collected by the nozzle through the first fluid path or the second fluid path.

2. A selective filtering system, comprising:
   a vacuum source;
   a suction nozzle assembly including a first suction port, a second suction port, a suction nozzle and a valve, said suction nozzle assembly additionally including a selector switch for actuating said valve to selectively communicate suction between said suction nozzle and said first suction port when said valve is in a first position, and to selectively communicate suction between said suction nozzle and said second suction port when said valve is in a second position;
   a bypass tube connected between said first suction port and said vacuum source; and
   a removable filter cartridge including an entry port and an exit port, said filter connected in parallel with said bypass tube, the entry port of said filter in communication with said second suction port and the exit port in communication with said vacuum source, said filter including a filter medium for collecting tissue;
   said removable filter cartridge including a filter cartridge housing including a back wall and a side wall, an inner chamber of a first diameter defined by the back wall and the side wall, an inner filter medium of a second diameter located within said inner chamber, said second diameter being smaller than said first diameter, and a plunger base slidably located inside the inner filter medium adjacent the back wall of said removable filter cartridge.

3. The selective filtering system of claim 2, wherein said removable filter cartridge additionally includes an annular bore through the back wall, said annular bore in communication with said plunger base, and a filter cap located at the front of said filter cartridge distal from the back wall, wherein said filter cap is removably engaged with the side wall of said filter cartridge housing.

4. The selective filtering system of claim 3, additionally including a delivery device, said delivery device including a delivery housing including a recess adapted to receive said filter cartridge housing, said delivery device including a front opening through the front of said recess and a ram at the rear of said recess, wherein said ram engages said plunger base through said annular bore to extrude bone material contained in said filter cartridge through said front opening.

5. The selective filtering system of claim 4, wherein said delivery device additionally includes a ratchet handle for reciprocating said ram through said annular bore.

6. In a bone collection system, a removable filter cartridge, comprising:
   a filter cartridge housing including a proximal end and a distal end separated by a side wall, said filter cartridge housing including a back wall located at the distal end of said housing, an inner chamber of a first diameter defined by the back wall and the side wall, said filter cartridge housing additionally including an exit port in communication with said inner chamber through the side wall, said filter cartridge housing additionally including a bore through the back wall;
   an inner filter medium located within said inner chamber in communication with said exit port, said inner filter medium comprising a mesh sized to capture bone material while permitting fluid passage through said mesh;
   a plunger base having a front surface and a back surface separated by a plunger base perimeter edge, said plunger base slidably located inside the inner chamber, the back surface of said plunger base adjacent the back wall of said removable filter cartridge and in communication with said bore; and
   a filter cap removably engaged with the proximal end of said filter cartridge housing, said filter cap including an entry port in communication with the inner chamber of said filter cartridge housing.

7. The system of claim 6, wherein the bone collection system includes a bone delivery device, said delivery device including a delivery housing including a recess adapted to receive said filter cartridge housing, said delivery device including a front opening through the front of said recess and a ram at the rear of said recess, wherein said ram engages said plunger base through said bore to extrude bone material contained in said filter cartridge through said front opening.

8. The system of claim 6, wherein said inner filter medium is a cylindrical filter cartridge having a second diameter, said second diameter being smaller than said first diameter, and wherein said plunger base includes a circular perimeter edge having a third diameter, said third diameter being smaller than said second diameter.

9. The system of claim 8, wherein said input port of said filter cartridge is in fluid communication with a suction nozzle assembly of the bone collection system, wherein said suction nozzle assembly includes a first suction port, a second suction port, a suction nozzle and a valve, said suction nozzle assembly additionally including a selector switch for actuating said valve to selectively communicate suction between said suction nozzle and said first suction port when said valve is in a first position, and to selectively communicate suction between said suction nozzle and said second suction port when said valve is in a second position, wherein said first suction port is connected to said filter cartridge and wherein said second suction port is connected to a bypass tube connected in parallel with said filter cartridge.

10. A method for harvesting bone from a surgical location, comprising:
    surgically generating collectable bone;
    providing a selective filtering system comprising:
      a suction nozzle assembly including a first suction port, a second suction port, a suction nozzle and a valve, said suction nozzle assembly additionally including a selector switch for actuating said valve to selectively communicate suction between said suction nozzle and said first suction port when said valve is in a first position, and to selectively communicate suction between said suction nozzle and said second suction port when said valve is in a second position;

a suction line including a proximal end and a distal end;

a bypass tube connected between said first suction port and the proximal end of said suction line;

a filter cartridge including an entry port and an exit port, said filter cartridge connected in parallel with said bypass tube, the entry port of said filter cartridge in communication with said second suction port and the exit port in communication with the proximal end of said suction line, said filter cartridge including a filter medium for collecting tissue;

wherein said filter cartridge further comprises:

a filter cartridge housing including a back wall and a side wall, an inner chamber of a first diameter defined by the back wall and the side wall, said back wall including a bore therethrough;

an inner filter medium of a second diameter located within said inner chamber, said second diameter being smaller than said first diameter;

a plunger base slidably located inside the inner filter medium adjacent the back wall of said removable filter cartridge, said bore in communication with said plunger base; and a filter cap located at the front of said filter cartridge distal from the back wall, wherein said filter cap is removably engaged with the sidewall of said filter cartridge housing;

positioning said suction nozzle to collect said collectable bone;

applying suction to the distal end of said suction line to suction materials including said collectable bone; and actuating said switch to selectively direct suction to one of said bypass tube and said filter to draw the materials through one of said bypass tube and said filter.

11. The method of claim 10, further comprising the step of:

removing said filter cartridge while suction is directed through said bypass tube.

12. The method of claim 11, further comprising the steps of:

removing said filter cartridge from said selective filtering system;

removing said filter cap from said filter cartridge;

placing said filter cartridge in a delivery device; and extruding bone material from said filter cartridge using said delivery device.

13. The method of claim 12 wherein said bone material is extruded back into the patient location.

14. The method of claim 12, wherein said delivery device includes:

a delivery housing including a recess adapted to receive said filter cartridge housing, a front opening through the front of said recess; and a ram at the rear of said recess, wherein said ram engages said plunger base through said bore to extrude bone material contained in said filter cartridge through said front opening.

15. The selective filtering system of claim 14, wherein said delivery device additionally includes a ratchet handle for reciprocating said ram through said bore.

16. A method for surgically treating and returning harvested autogenous bone to a patient at a surgical site, comprising:

(a) surgically generating collectable bone at a surgical site of the patient;

(b) providing a selective filtering system comprising:

a suction nozzle assembly adapted to be held in the hand of a user, the suction nozzle assembly including a first suction port, a second suction port, a suction nozzle and a valve, said suction nozzle assembly additionally including a selector switch for actuating said valve to selectively communicate suction between said suction nozzle and said first suction port when said valve is in a first position, and to selectively communicate suction between said suction nozzle and said second suction port when said valve is in a second position;

a suction line including a proximal end and a distal end;

a bypass tube connected between said first suction port and the proximal end of said suction line;

a filter cartridge including an entry port and an exit port, said filter cartridge connected in parallel with said bypass tube, the entry port of said filter cartridge in communication with said second suction port and the exit port in communication with the proximal end of said suction line, said filter cartridge including a filter medium adapted to collect bone tissue and allowing fluids to pass;

(c) manipulating said suction nozzle assembly by hand so as to position said suction nozzle to collect said collectable bone from the surgical site;

(d) applying suction to the distal end of said suction line to suction tissue materials including soft tissue and said collectable bone;

(e) actuating said switch by hand to selectively direct suction to one of said bypass tube and said filter cartridge to draw the tissue materials through one of said bypass tube and said filter cartridge, wherein drawing the materials through said filter cartridge results in collected bone within the filter cartridge, and wherein said actuating is conducted effectively to reduce the amount of soft tissue collected in said filter cartridge along with said collected bone; and (f) implanting the collected bone at the surgical site of the patient.

* * * * *